United States Patent [19]

Warriner

[11] Patent Number: Plant 6,445

[45] Date of Patent: Dec. 6, 1988

[54] ROSE PLANT JACHY

[75] Inventor: William A. Warriner, Tustin, Calif.

[73] Assignee: Jackson & Perkins Co., Medford, Oreg.

[21] Appl. No.: 936,008

[22] Filed: Nov. 28, 1986

[51] Int. Cl.[4] ..... A01H 5/00

[52] U.S. Cl. ..... Plt./15

[58] Field of Search ..... Plt./15

*Primary Examiner*—James R. Feyrer

*Attorney, Agent, or Firm*—Majestic, Gallagher, Parsons & Siebert

[57] ABSTRACT

A hybrid tea rose variety having shiny, dark green foliage; large, bright yellow flowers; golden yellow buds; vigorous, upright growth; and long vase life. The variety is also susceptible to powdery mildew in Irvine, Calif.

1 Drawing Sheet

This present invention relates to a new and distinct variety of rose plant of the hybrid tea class which was originated by crossing the variety Sunbright, U.S. Plant Pat. No. 4,438, with the variety Medallion, U.S. Plant Pat. No. 2,997.

The primary objective of this breeding was to produce a new rose variety of the hybrid tea class exhibiting large, bright yellow flowers borne on a strong upright bush. This objective was substantially achieved along with other desirable improvements as evidenced by the following unique combination of characteristics which are outstanding in the new variety and which distinguish it from its parents as well as from all other varieties of which I am aware:

1. Deep, golden yellow bud;
2. Bright yellow, large open flower;
3. Upright, vigorous habit of growth;
4. Long vase life;
5. Powdery mildew susceptibility; and
6. Dark green glossy foliage.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Sunbright, U.S. Plant Pat. No. 4,438.

*Pollen parent.*—Medallion, U.S. Plant Pat. No. 2,997.

Classification:

*Botanical.*—Rosa hybrid.

*Commercial.*—Hybrid tea.

FLOWER

Observations made from specimens grown in a greenhouse at Irvine, Calif. in September and October, 1986.

Blooming habit: Continuous.

Bud:

*Size.*—1½ to 2" when petals start to unfurl.

*Form.*—Long, pointed ovoid.

*Color.*—When sepals first divide, Yellow-Orange Group 15A to B with an occasional pinkish blush on outer petals; when half blown, upper side of petals becoming bright yellow (Yellow Group 12A); lower side of petals, bright yellow (Yellow Group 12A).

*Sepals.*—Color: Green Group 137D. Three appendaged sepals heavily appendaged. Two unappendaged sepals hairy edged.

*Receptacle.*—Color: Green Group 137D with a bronze blush. Shape: Funnel. Size: Medium. Surface: Smooth.

*Peduncle.*—Length: Medium. Surface: Prickly. Color: Medium green with a bronzy blush. Strength: Stiff.

Open bloom:

*Size.*—Large. Average open size 5".

*Borne.*—Singly.

*Stems.*—Medium, strong.

*Form.*—When first open, high center. Permanence: Flattens slightly, outer petal edges slightly curled.

*Petalage.*—Number of petals under normal conditions: 30–35.

*Color.*—Center of flower: Upper side of petals, Yellow Group 12A; reverse side of petals, Yellow Group 12A. Base of petals, Yellow Group 12A. Major color: Yellow Group 12A.

*Variegations.*—None.

*Discoloration.*—General tonality at end of first day: None. Third day: Some fading — particularly in hot sunny weather.

*Fragrance.*—Slight.

Petals:

*Texture.*—Thick.

*Shape.*—Obovate and occasionally notched.

*Form.*—Flat, tips slightly recurved.

*Arrangement.*—Imbricated.

*Persistence.*—Drop off cleanly.

*Lastingness.*—On the plant, long. As cut flower, long.

Reproductive parts:

*Anthers.*—Large. Color: Yellow. Arrangement: Regular around styles. Some anthers, in all flowers examined, will be blackened while the other anthers are a bright yellow. This suggests some pollen abortion may be occurring.

*Filaments.*—Color: Yellow.

*Pollen.*—Gold yellow.

*Styles.*—Color: Red.

*Stigmas.*—Color: Greenish white.

PLANT

Form: Bush.

Growth: Vigorous.

Foliage:

*Number of leaflets on normal mid-stem leaves.*—5 to 7.

*Size.*—Large.

*Quantity.*—Normal.

*Color.*—New foliage: Reddish. Old foliage: Dark green (Green Group 139A).

Leaflets:

*Shape.*—Oval pointed.

*Texture.*—Leathery.

*Edge.*—Serrated.

*Serration.*—Single.

*Petiole.*—Rachis: Color: Green. Underside: Smooth, with prickles.

*Stipules.*—Medium bearded.

*Disease resistance.*—Susceptible to mildew under normal growing conditions at Irvine, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Straight to hooked slightly downward.

*Color when young.*—Red.

Small prickles:

*Quantity.*—On main stalks, none. On laterals, none.

I claim:

1. A new and distinct variety of rose plant and parts thereof of the hybrid tea class, substantially as herein shown and described, characterized particularly as to novelty by the unique combination of shiny, dark green foliage; large, bright yellow flowers; golden yellow buds; vigorous, upright growth; long vase life; and susceptibility to powdery mildew in Irvine, Calif.

* * * * *

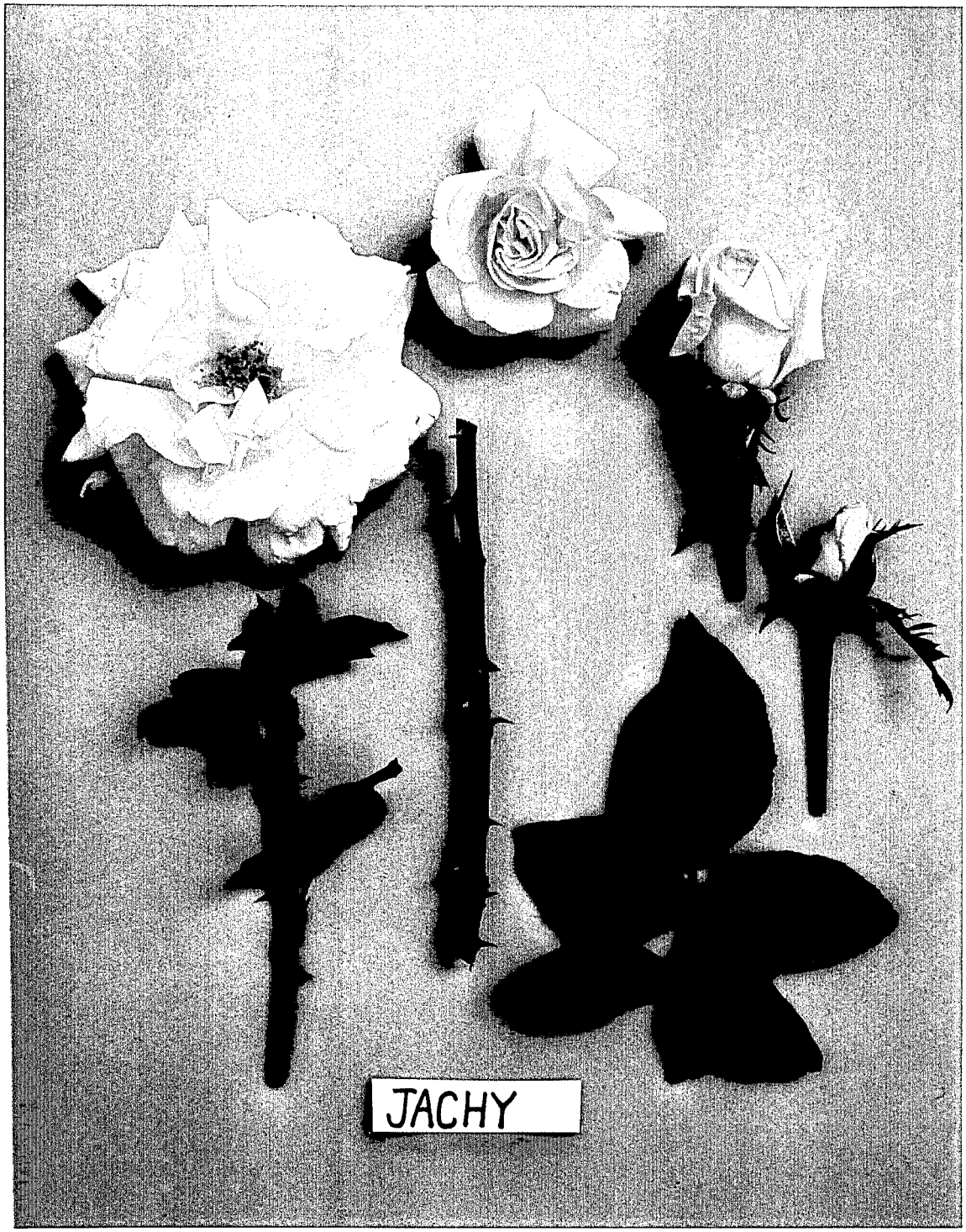
JACHY